| United States Patent [19] | [11] Patent Number: 4,977,139 |
| Yamada et al. | [45] Date of Patent: Dec. 11, 1990 |

[54] AQUEOUS ELCATONIN SOLUTION COMPOSITION

[75] Inventors: Hitoshi Yamada; Ken Endo; Kikuo Kotani, all of Shizuoka, Japan

[73] Assignee: Toyo Jozo Company, Ltd., Shizuoka, Japan

[21] Appl. No.: 427,597

[22] Filed: Oct. 25, 1989

[30] Foreign Application Priority Data

Dec. 23, 1988 [JP] Japan ................... 63-324999

[51] Int. Cl.$^5$ ............................. A61K 37/00
[52] U.S. Cl. ..................... 514/11; 514/808; 514/970
[58] Field of Search .............. 514/808, 2, 784, 970

[56] References Cited

U.S. PATENT DOCUMENTS 4,086,221  4/1978  Sakakibara et al. ............ 514/808
4,690,952  9/1987  Kagatani et al. ............... 514/808

OTHER PUBLICATIONS

Handbook of Chemistry and Physics, 57th edition (1976), p. D–135.

*Primary Examiner*—Douglas W. Robinson
*Assistant Examiner*—Raymond J. Henley, III
*Attorney, Agent, or Firm*—Darby & Darby

[57] ABSTRACT

The present invention provides an aqueous solution composition containing elcatonin as an active ingredient used for hypercalcemia or bone Paget's disease or improvement of pain in osteoporosis, etc. and which is highly stable against shaking, light and heat. This composition contains an effective amount of elcatonin as an active ingredient and a monocarboxy compound and/or its water soluble salt thereof in a molar concentration of 0.05–20 mmol and has a pH of 5.0–6.5 and an ionic strength of $\mu=0.01$–0.5. Preferred examples of the monocarboxy compound and its salts are acetic acid, lactic acid, L-histidine, sodium acetate, potassium acetate, sodium lactate, potassium lactate and L-histidine hydrochloride.

5 Claims, No Drawings

AQUEOUS ELCATONIN SOLUTION COMPOSITION

BACKGROUND OF THE INVENTION

The present invention relates to an aqueous solution composition containing elcatonin as an active ingredient.

Elcatonin is a medicine having chemical name: 1-butyric acid-7-(L-2-aminobutyric acid)-26- o L-aspartic acid-27-L-valine-29-L-alanine-calcitonin (salmon) and is used for hypercalcemia or bone Paget's disease, or improvement of pain in osteoporosis. Activity of elcatonin is sometimes reduced owing to vigorous shaking when it is made to a preparation in the form of aqueous solution and it is not necessarily satisfactory as preparation which is to be stable against shaking.

Under such circumstance that mechanism of reduction in activity of aqueous solution of peptide owing to shaking has not been elucidated, the inventors have conducted intensive research in an attempt to maintain the present status of heat stability and light stability of elcatonin in the form of injections or further improve them and besides to maintain the present status of reduction of pain or further reduce the pain at injection. Furthermore, there has been reported that reduction in activity of aqueous solution of peptide caused by shaking can be prevented by adding a surface active agent, but there has been the problem in safety. Under the circumstances, the inventors have made further research in an attempt to solve the problem of reduction in activity without addition of surface active agent.

As a result, the inventors have found that an injection composition comprising an aqueous solution composition containing elcatonin as an active ingredient which has high stability of elcatonin against shaking can be obtained by adding a monocarboxy compound and/or its water-soluble salt in an amount of 0.05-20 mmol in molar concentration and adjusting pH to 5.0-6.5 and ionic strength to $\mu=0.01-0.5$ and the resulting composition is no less better than conventional compositions in heat stability and light stability as an injection and in reduction of pain at injection.

SUMMARY OF THE INVENTION

The present invention has been accomplished based on the above finding.

That is, the present invention relates to an aqueous elcatonin solution composition containing elcatonin as an active ingredient which contains a monocarboxy compound and/or its water-soluble salt in a molar concentration of 0.05-20 mmol and has a pH of 5.0-6.5 and an ionic strength of $\mu=0.01-0.5$.

DESCRIPTION OF THE INVENTION

According to the main process for preparation of the aqueous elcatonin solution composition of the present invention, stabilized elcatonin injection composition can be obtained by dissolving an effective amount of elcatonin in an aqueous medium which contains a monocarboxy compound and/or its water-soluble salt in a molar concentration of 0.05-20 mmol and has a pH of 5.0-6.5 and an ionic strength of $\mu=0.01-0.5$. In more detail, an aqueous medium is prepared by adjusting pH with a buffer solution containing monocarboxylic acid and/or its water-soluble salt and further calculating ionic strength thereof, if necessary, with addition of non-toxic strong electrolyte inorganic salts such as sodium chloride and potassium chloride to adjust ionic strength and furthermore an effective amount of elcatonin which is an active ingredient is dissolved in the aqueous medium. This is a simple and convenient process. Effective amount of elcatonin may be dissolved optionally at the step of preparation of the aqueous medium and the sequence of preparation should not be specified. Furthermore, if necessary, there may be added other formulation components such as isotonicity imparting agent, pain removing agent, stabilizing agent, absorption accelerating agent and preservative.

The buffer solution containing monocarboxy compound and/or its water-soluble salt is a buffer solution containing monocarboxy compound and/or its water-soluble salt which can be added for medical treatment and this buffer solution should have such buffering action to keep pH of final composition within the range of 5.0-6.5. The monocarboxy compound or its salt which can be added for medical treatment is an organic compound having one carboxyl group in its molecule or a salt thereof. Preferred examples thereof are acetic acid, lactic acid, and L-histidine and salts thereof such as sodium acetate, potassium acetate, sodium lactate, potassium lactate and L-histidine hydrochloride. Especially preferred are acetic acid and its salts. The pH of final composition is adjusted to 5.0-6.5 by adding one or more of the monocarboxy compound and/or its salt and, if necessary, fine adjustment of pH may be made with sodium hydroxide, hydrochloric acid, etc. The pH buffer may be used in a minimum amount capable of buffering pH of the aqueous elcatonin solution composition to 5.0-6.5 and when this composition is used for injection, etc., amount (in molar concentration) of the buffer is 0.05-20 mmol, more preferably 0.1-5 mmol.

Ionic strength which is calculated by the following calculation formula is adjusted to $\mu=0.01-0.5$, if necessary, with addition of sodium chloride, potassium chloride etc. and it is preferred to adjust it to $\mu=0.04-0.3$. If the ionic strength is less than 0.01, the desired stability cannot be sufficiently attained and if it is more than 0.5, the composition causes stimulus at the tissue where the composition is administered.

$\mu=\frac{1}{2}\Sigma r_i \cdot z_i^2$: molar concentration of ion and $z_i$:its ionic charge value)

When sodium chloride, potassium chloride or the like is added, amount thereof is preferably 0.2-1.2 %. Effective content of elcatonin which is an active ingredient is, or example, 1-100 μg per 1 ml of solution, preferably 1-10 μg per 1 ml of solution in case of injections and 1-100 μg per 1 ml of solution in case of preparation to be administered through nose.

The thus obtained composition can be formulated as aqueous preparations for injections or administration through nose in conventional manner by pouring it in a glass or plastic container for medicines such as an ampule, vial or the like. However, if water or acid acts on the inner surface of container made of, for example borosilicate glass or soda-lime glass, pH of aqueous solution composition may vary due to external factors such as dissolving out of alkali component from the inner surface. In this case, for selective washing and removal of alkali component in the surface portion of glass container, it is desired to use a container which has been subjected to special processing such as a treatment for removal of alkali which comprises contacting glass surface kept at a high temperature of about 250°-800° C. with a water-soluble sulfur oxide such as sulfur dioxide or ammonium sulfate to convert the alkali component of the surface to fine sulfate crystal and then washing the surface or a special container which brings about no variation of pH due to external factors.

The thus obtained aqueous elcatonin solution composition has stability of elcatonin against shaking and besides, is no less better than conventional products in heat stability and light stability as injections and in reduction of pain caused by injection.

The present invention will be explained by the following examples which never limit the present invention.

EXAMPLE 1

0.544 g of sodium acetate (trihydrate) and 1.8 g of sodium chloride were dissolved in water to prepare 200 ml of a solution. This solution was referred to as solution A. Separately, 0.24 g of acetic acid and 1.8 g of sodium chloride were dissolved in water to prepare 200 ml of a solution. This was referred to as solution B. 200 ml of solution A was mixed with 25 ml of solution B to adjust pH to 5.5 and ionic strength to 0.17. In 200 ml of the resulting solution was dissolved 1.4 mg of elcatonin to obtain an aqueous elcatonin solution composition. Then, 1 ml of this aqueous elcatonin solution composition was filled in 1 cc glass ampule to obtain an injection containing 7 μg of elcatonin.

EXAMPLE 2

0.544 g of sodium acetate (trihydrate) and 1.8 g of sodium chloride were dissolved in water to obtain 200 ml of a solution. 1 ml of this solution was diluted with 0.9 % (w/v) sodium chloride solution to 200 ml. This solution was adjusted to pH 5.5 and ionic strength 0.15 by adding thereto 0.7 ml of 0.002N hydrochloric acid. In 200 ml of the resulting solution was dissolved 1.4 mg of elcatonin to obtain an aqueous elcatonin solution composition. Since the pH buffer solution of the aqueous elcatonin solution composition was dilute and variation of pH is liable to occur when it is filled in a normal glass ampule, 1 ml of the aqueous elcatonin solution composition was filled in a 1 cc glass ampule which had been subjected to a treatment for removal of alkali (by contacting 0.5 % aqueous ammonium sulfate solution with the surface of inner wall of the ampule kept at about 600° C., then subjecting the ampule to ultrasonic cleaning, washing with distilled water for injection and drying at 250° C.), thereby to obtain an injection containing 7 μg of elcatonin. Operation was conducted under sterile condition in both Examples 1 and 2.

EXAMPLES 3-5

Aqueous elcatonin solution compositions as shown in Table 1 using various monocarboxy compounds and/or their salts and injections containing 7 μg of elcatonin were prepared in the same manner as in Examples 1 and 2.

CONTROL EXAMPLES A-D

Aqueous elcatonin solution compositions outside the present invention were prepared as controls and injections containing 7 μg of elcatonin were prepared in the same manner as above. The compositions and others are shown in Table 1.

TABLE 1

| Example, Control Example | Composition | Concentration of composition | pH | Ionic strength | Note |
|---|---|---|---|---|---|
| 1 | Elcatonin | 7 μg/ml | 5.5 | 0.17 | |
|   | Sodium acetate | 17.8 mM | | | |
|   | Acetic acid | 2.2 mM | | | |
|   | Sodium chloride | 154 mM | | | |
| 2 | Elcatonin | 7 μg/ml | 5.5 | 0.15 | Ampule was subjected to treatment for removal of alkali |
|   | Sodium acetate | 0.1 mM | | | |
|   | Hydrochloric acid | Slight amount | | | |
|   | Sodium chloride | 154 mM | | | |
| 3 | Elcatonin | 7 μg/ml | 5.5 | 0.17 | |
|   | Sodium DL-lactate | 20.0 mM | | | |
|   | Hydrochloric acid | Slight amount | | | |
|   | Sodium chloride | 154 mM | | | |
| 4 | Elcatonin | 7 μg/ml | 5.5 | 0.27 | Ampule was subjected to treatment for removal of alkali |
|   | Sodium DL-lactate | 0.1 mM | | | |
|   | Hydrochloric acid | Slight amount | | | |
|   | Sodium chloride | 268 mM | | | |
| 5 | Elcatonin | 7 μg/ml | 5.5 | 0.17 | |
|   | L-histidine hydrochloride | 20.0 mM | | | |
|   | NaOH | 3.5 mM | | | |
|   | Sodium chloride | 154 mM | | | |
| A | Elcatonin | 7 μg/ml | 5.5 | 0.21 | |
|   | Sodium succinate | 20.0 mM | | | |
|   | Hydrochloric acid | 6.5 mM | | | |
|   | Sodium chloride | 154 mM | | | |
| B | Elcatonin | 7 μg/ml | 5.5 | 0.21 | |
|   | Sodium tartrate | 20.0 mM | | | |
|   | Hydrochloric acid | Slight amount | | | |
|   | Sodium chloride | 154 mM | | | |
| C | Elcatonin | 7 μg/ml | 5.5 | 0.24 | |
|   | Sodium succinate | 16.3 mM | | | |
|   | Succinic acid | 3.7 mM | | | |

TABLE 1-continued

| Example, Control Example | Composition | Concentration of composition | pH | Ionic strength | Note |
| --- | --- | --- | --- | --- | --- |
| D | Sodium chloride<br>Elcatonin<br>Sodium succinate<br>Hydrochloric acid<br>Sodium chloride | 154 mM<br>7 μg/ml<br>0.1 mM<br>Slight amount<br>154 mM | 5.5 | 0.15 | Ampule was subjected to treatment for removal of alkali |

| NaCl concentration | Ionic strength | Residual rate (%) |
| --- | --- | --- |
| 3 mM | 0.003 | 50 |
| 10 mM | 0.010 | 79 |
| 154 mM | 0.154 | 98 |
| 500 mM | 0.500 | 97 |

TEST EXAMPLE 1

Elcatonin injections containing the aqueous elcatonin solution composition of the present invention obtained in Examples 1-5 and elcatonin injections containing the aqueous elcatonin solution composition outside the present invention obtained in Control Examples A-D were put in a box made of paper and were shaken in a constant temperature shaking machine. Stability was measured by high performance liquid chromatography to obtain residual rate of elcatonin. The results are shown in Table 2.

Shaking conditions were as follows

Shaking width: 10 cm
Shaking rate: 120 times/min
Temperature: 25° C.

Conditions for measurement by high performance liquid chromatography

Column: ODS column 4.6 × 150 mm
Detection: UV 220 nm
Mobile phase: $CH_3CN$-0.1 % TFA (34:66)

TABLE 2

| Example, Control Example | Residual rate after each shaking time (%) | | |
| --- | --- | --- | --- |
| | 3 days | 7 days | 14 days |
| 1 | 97 | 102 | 95 |
| 2 | 103 | 104 | 96 |
| 3 | 94 | 99 | 92 |
| 4 | 98 | 97 | 100 |
| 5 | 99 | 95 | 95 |
| A | 102 | 86 | 61 |
| B | 94 | 83 | 49 |
| C | 98 | 83 | 39 |
| D | 98 | 90 | 67 |

From the above results, it can be seen that the aqueous elcatonin solution compositions of the present invention were very stable against shaking.

TEST EXAMPLE 2

In preparation of 0.1 mM sodium acetate pH buffer of pH 5.5 in Example 2, four kinds of solutions were prepared so that concentration of sodium chloride was 3 mM, 10 mM, 154 mM and 500 mM. Elcatonin was dissolved therein so that elcatonin concentration was 7 μg/ml. Each of the compositions was filled in an ampule in the same manner as in Example 1 to prepare elcatonin injections having four kinds of ionic strength. The resulting elcatonin injections were stored at 45° C. for 3 months and residual rate was obtained under the same conditions as in Test Example 1. The results are shown below.

As in the above table, severe test against heat showed that elcatonin injections having an ionic strength of 0.01-0.500 were stable against heat.

EXAMPLE 6

An aqueous elcatonin solution composition of the present invention containing 10 μg/ml of elcatonin, 0.1 mM of sodium acetate and 100 mM of potassium chloride was prepared and thereto was added methylparaben in an amount of 1 % as a preservative. 3 ml of this composition was filled in a small bottle for administration through nose.

This was tested on stability against shaking in the same manner as in Test Example 1 to find that it was stable against shaking for 7 days and was also stable against the severe test to heat as in Test Example 2.

As explained above, the present invention provides a good aqueous elcatonin solution composition which is stable against shaking and is also stable to heat and light.

We claim:

1. An aqueous elcatonin solution composition which contains an effective amount of elcatonin as an active ingredient and at least one compound selected from the group consisting of at least one of acetic acid, lactic acid, L-histidine and water soluble salts thereof in a molar concentration within the range of from 0.05 to 20 mmol and which has a pH within the range of from 5.0 to 6.5 and an ionic strength within the range of from 0.01 to 0.3, said composition being stabilized against shaking.

2. An aqueous elcatonin solution composition according to claim 1, wherein the salt is selected from the group consisting of sodium acetate, potassium acetate, sodium lactate, potassium lactate and L-histidine hydrochloride.

3. An aqueous elcatonin solution composition according to claim 1, wherein the content of the elcatonin is within the range of from 1 to 100 μg per 1 ml of solution.

4. The composition according to claim 1 wherein the composition is in an injectable dosage form.

5. A process for preparation of an aqueous elcatonin solution composition stabilized against shaking which comprises dissolving an effective amount of elcatonin in an aqueous medium containing at least one compound selected from the group consisting of at least one of acetic acid, lactic acid, L-histidine and a salt thereof in a molar concentration within the range of from 0.05 to 20 mmol and having a pH within the range of from 5.0 to 6.5 and an ionic strength within the range of from 0.01 to 0.3 .

* * * * *

UNITED STATES PATENT AND TRADEMARK OFFICE
CERTIFICATE OF CORRECTION

PATENT NO. : 4,977,139

DATED : December 11, 1990

INVENTOR(S) : Hitoshi Yamada, Ken Endo, and Kikuo Kotani

It is certified that error appears in the above-identified patent and that said Letters Patent is hereby corrected as shown below:

Column 4, TABLE 1, in Example, Control Example C, Column entitled Composition:
Delete "Sodium succinate" and insert --Sodium citrate-- and delete "Succinic acid" and insert --Citric acid--.

Column 5, TABLE 1 - continued, in Example, Control Example D, Column entitled Composition:
Delete "Sodium succinate" and insert --Sodium citrate--.

Signed and Sealed this

Thirtieth Day of June, 1992

*Attest:*

DOUGLAS B. COMER

*Attesting Officer*     *Acting Commissioner of Patents and Trademarks*